(12) United States Patent
Bahn et al.

(10) Patent No.: US 8,933,186 B2
(45) Date of Patent: Jan. 13, 2015

(54) POLYORGANOSILOXANE, POLYCARBONATE RESIN COMPOSITION COMPRISING THE SAME AND MODIFIED POLYCARBONATE RESIN

(71) Applicant: LG Chem, Ltd., Seoul (KR)

(72) Inventors: Hyong Min Bahn, Daejeon (KR); Moo Ho Hong, Daejeon (KR); Young Young Hwang, Daejeon (KR); Min Jeong Kim, Daejeon (KR); Jung Jun Park, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 14/240,005

(22) PCT Filed: Feb. 1, 2013

(86) PCT No.: PCT/KR2013/000844
§ 371 (c)(1),
(2) Date: Feb. 20, 2014

(87) PCT Pub. No.: WO2013/115604
PCT Pub. Date: Aug. 8, 2013

(65) Prior Publication Data
US 2014/0206802 A1    Jul. 24, 2014

(30) Foreign Application Priority Data

Feb. 3, 2012  (KR) .................. 10-2012-0011519
Feb. 1, 2013  (KR) .................. 10-2013-0011704

(51) Int. Cl.
*C08G 77/448*  (2006.01)
*C07F 7/08*   (2006.01)
*C08G 77/14*  (2006.01)
*C08K 5/5419* (2006.01)

(52) U.S. Cl.
CPC .............. *C07F 7/0852* (2013.01); *C08G 77/14* (2013.01); *C08K 5/5419* (2013.01)
USPC .................... 528/25; 528/29; 528/31; 528/37

(58) Field of Classification Search
None
See application file for complete search history.

(56) References Cited

U.S. PATENT DOCUMENTS

| 5,130,460 | A  |   | 7/1992  | Kamei et al. |
| 5,243,009 | A  | * | 9/1993  | Rich et al. ........................ 528/26 |
| 5,552,506 | A  | * | 9/1996  | Ebbrecht et al. ................ 528/15 |
| 5,726,271 | A  |   | 3/1998  | Furukawa et al. |
| 6,630,562 | B2 | * | 10/2003 | Ogawa et al. ................. 528/196 |
| 7,232,865 | B2 |   | 6/2007  | DeRudder et al. |

FOREIGN PATENT DOCUMENTS

| JP | 2011-122048    | 6/2011 |
| KR | 10-2002-0016922 | 3/2002 |
| KR | 10-2005-0092727 | 9/2005 |
| KR | 10-2007-0072325 | 7/2007 |
| KR | 10-2008-0056204 | 6/2008 |

\* cited by examiner

*Primary Examiner* — Marc Zimmer
(74) *Attorney, Agent, or Firm* — McKenna Long & Aldridge, LLP

(57) ABSTRACT

Disclosed are novel polyorganosiloxane, a polycarbonate resin composition comprising the same and a modified polycarbonate resin. Disclosed is also a novel polyorganosiloxane derivative which may be utilized in various applications and is used in particular as an impact modifier, a modifier or a comonomer of polycarbonate resin.

10 Claims, 1 Drawing Sheet

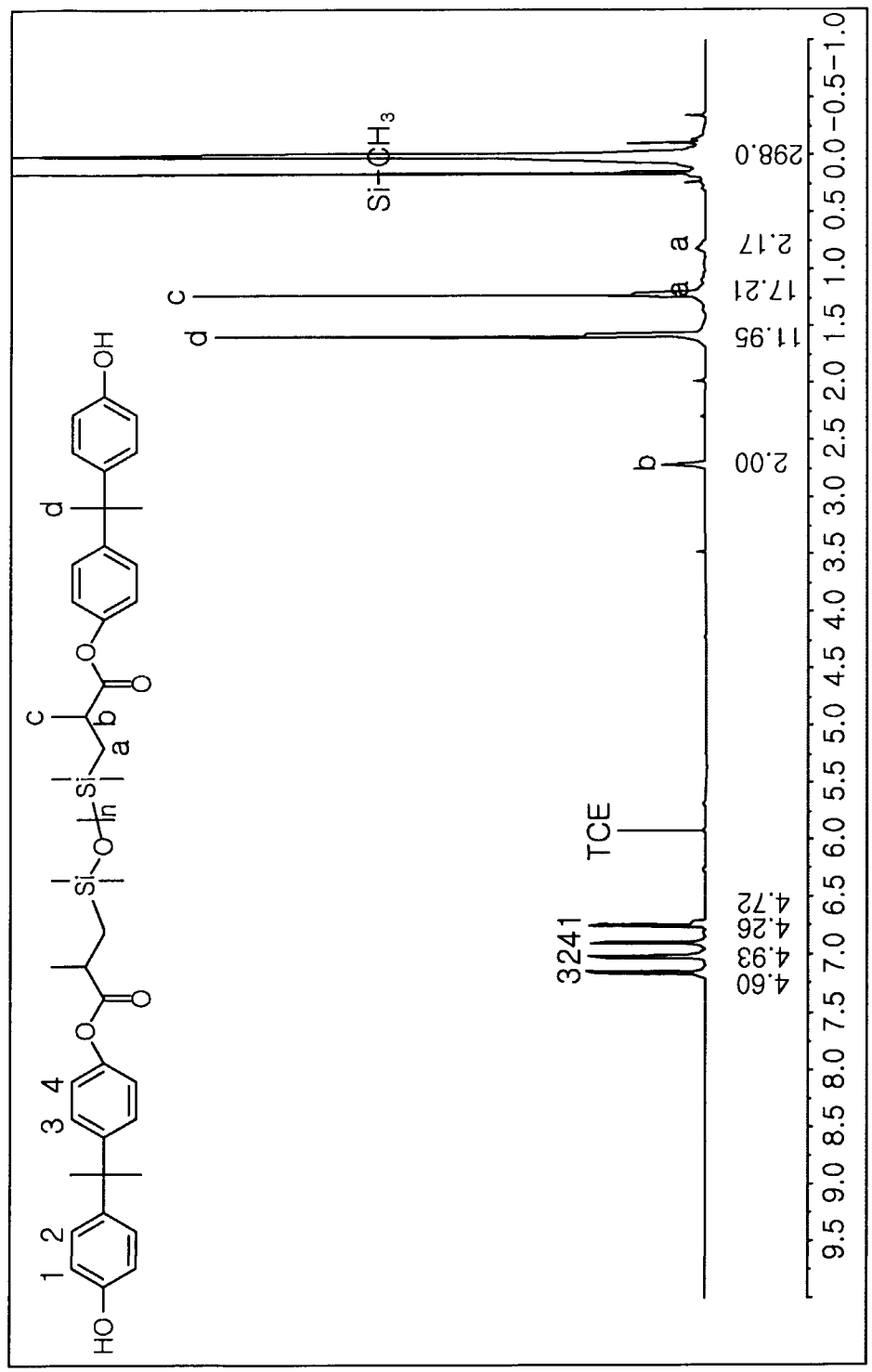

POLYORGANOSILOXANE, POLYCARBONATE RESIN COMPOSITION COMPRISING THE SAME AND MODIFIED POLYCARBONATE RESIN

This application is a National Phase of International Application PCT/KR2013/000844, with an international filing date of Feb. 1, 2013, which claims priority to and the benefit of Korean Patent Application No. 10-2012-0011519, filed on Feb. 3, 2012, and Korean Patent Application No. 10-2013-0011704, filed on Feb. 1, 2013, all of which are incorporated herein by reference in their entirety.

TECHNICAL FIELD

The present invention relates to novel polyorganosiloxane. More specifically, the present invention relates to novel polyorganosiloxane which may be utilized for a variety of applications and is used in particular as an impact reinforcing agent, a modifier or a comonomer of polycarbonate resins.

BACKGROUND ART

Polyorganosiloxane is a kind of silicone which is a polymer having a siloxane linkage substituted by organic groups as a backbone. Polyorganosiloxane is colorless and odorless, is slow to oxidize, is a hypoallergenic insulator stable even at room temperature and is used for electrical and electronic equipment, automobiles, machinery, medicines, cosmetics, lubricants, adhesives, gaskets, plastic artificial aids and the like.

In the related art, KR Patent Laid-open No. 2002-0016922 (published on Mar. 6, 2002) discloses polyorganosiloxanes endcapped with trimethylsilyl useful as hydrogel contact lens materials.

DISCLOSURE

Technical Problem

Therefore, the present invention has been made in view of the above problems, and it is an object of the present invention to provide a novel polyorganosiloxane derivative which may be utilized for a variety of applications, in particular, which is useful as an impact reinforcing agent, a modifier or a comonomer of polycarbonate resins.

The object described above and other objects of the present invention can be accomplished by the present invention described below.

Technical Solution

In accordance with one aspect of the present invention, provided is novel polyorganosiloxane represented by Formula 1 below:

[Formula 1]

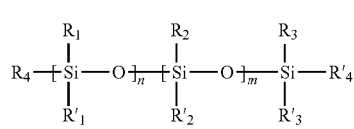

wherein $R_1$ to $R_3$ and $R'_1$ to $R'_3$ represent $CH_3$— or $C_6H_5$—, $R_4$ represents

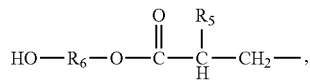

$R'_4$ represents $CH_3$—, $C_6H_5$— or

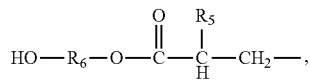

$R_5$ represents H or $CH_3$—, $R_6$ represents a $C_6$-$C_{20}$ arylene group or a $C_7$-$C_{20}$ alkylarylene group, and n and m are integers with the proviso of $0 \leq n+m \leq 99$.

In accordance with another aspect of the present invention, provided is a method of preparing a polyorganosiloxane comprising a) reacting organodisiloxane with organocyclosiloxane in the presence of an acid catalyst to prepare unmodified polyorganosiloxane, and b) reacting the prepared unmodified polyorganosiloxane with a hydroxy aryl (meth)acrylate compound or a hydroxy alkylaryl (meth)acrylate compound in the presence of a metal catalyst to prepare end-modified polyorganosiloxane.

In accordance with another aspect of the present invention, provided is a modified polycarbonate resin modified with the polyorganosiloxane.

In accordance with another aspect of the present invention, provided is a polycarbonate resin composition comprising the polyorganosiloxane and a polycarbonate resin.

Effects of the Invention

As apparent from the fore-going, the present invention has an effect of providing a novel polyorganosiloxane derivative which may be utilized for a variety of applications, in particular, which is useful as an impact reinforcing agent, a modifier or a comonomer of polycarbonate resins.

DESCRIPTION OF DRAWINGS

The above and other objects, features and other advantages of the present invention will be more clearly understood from the following detailed description taken in conjunction with the accompanying drawings, in which:

FIG. 1 is a ¹H NMR spectrum of BPMA-PDMS prepared in Example 1. TCE in the spectrum means a 1,1,2,2,-tetrachloroethane solvent used for measurement.

BEST MODE

Hereinafter, the present invention will be described in detail.

The novel polyorganosiloxane according to the present invention is characterized by a compound represented by Formula 1 below:

Formula 1

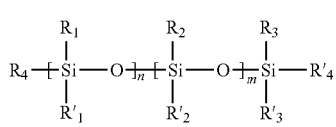

wherein $R_1$ to $R_3$ and $R'_1$ to $R'_3$ represent $CH_3$— or $C_6H_5$— (phenyl), $R_4$ represents

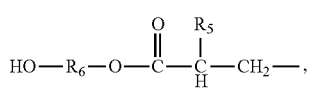

R'$_4$ represents CH$_3$—, C$_6$H$_5$— or

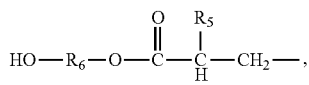

R$_5$ represents H or CH$_3$—, R$_6$ represents a C$_6$-C$_{20}$ arylene group or a C$_7$-C$_{20}$ alkylarylene group, and n and m are integers with the proviso of 0≤n+m≤99.

For example, R$_6$ represents a C$_6$-C$_{20}$ arylene group or a C$_7$-C$_{20}$ alkylarylene group. Alternatively, R$_6$ represents phenylene, diphenylene or dialkylphenylene. In this case, impact strength is greatly improved without greatly affecting heat resistance when the compound is applied to polycarbonate resins.

For example, m+n is preferably 0 to 99, 20 to 70, 25 to 60 or 35 to 55 in that mechanical properties are greatly improved without impairing transparency when the compound is applied to polycarbonate resins.

For example, m and n are integers of 0 or higher.

The polyorganosiloxane is preferably used as at least one selected from the group consisting of comonomers, modifiers and impact reinforcing agents.

The polyorganosiloxane is preferably applied to a polycarbonate resin. In this case, low-temperature impact strength can be improved while transparency of the polycarbonate resin is not impaired.

In an embodiment, a method of preparing the polyorganosiloxane according to the present invention comprises a) reacting organodisiloxane with organocyclosiloxane in the presence of an acid catalyst to prepare unmodified polyorganosiloxane, and b) reacting the prepared unmodified polyorganosiloxane with a hydroxy aryl (meth)acrylate compound or a hydroxy alkylaryl (meth)acrylate compound in the presence of a metal catalyst to prepare end-modified polyorganosiloxane.

In addition, the organodisiloxane for example comprises at least one selected from the group consisting of tetramethyldisiloxane, tetraphenyldisiloxane, hexamethyldisiloxane and hexaphenyldisiloxane.

The organodisiloxane is for example used in an amount of 0.1 to 10 parts by weight or 2 to 8 parts by weight, based on 100 parts by weight of the organocyclosiloxane.

The organocyclosiloxane is for example organocyclotetrasiloxane and is for example octamethylcyclotetrasiloxane, octaphenylcyclotetrasiloxane or the like.

Any acid catalyst may be used without particular limitation so long as it may be used for polyorganosiloxane synthesis and for example, the acid catalyst comprises at least one selected from the group consisting of H$_2$SO$_4$, HClO$_4$, AlCl$_3$, SbCl$_5$, SnCl$_4$ and acid clay.

The acid catalyst is for example 0.1 to 10 parts by weight, 0.5 to 5 parts by weight, or 1 to 3 parts by weight, based on 100 parts by weight of the organocyclosiloxane.

Any metal catalyst may be used without limitation so long as it may be useful for reaction of polysiloxane with a (meth)acrylate compound. The metal catalyst may, for example, be a Pt catalyst. Any Pt catalyst may be used without particular limitation so long as it may be used for polyorganosiloxane synthesis. Specifically, the Pt catalyst comprises at least one selected from the group consisting of an Ashby catalyst, a Karstedt's catalyst, a Lamoreaux catalyst, a Speier catalyst, PtCl$_2$(COD), PtCl$_2$(benzonitrile)$_2$ and H$_2$PtBr$_6$.

The metal catalyst is for example present in an amount of 0.001 to 1 part by weight, 0.005 to 0.1 parts by weight, or 0.01 to 0.05 parts by weight, based on 100 parts by weight of the organocyclosiloxane.

The aryl group of the hydroxy aryl (meth)acrylate compound or the hydroxy alkylaryl (meth)acrylate compound is, for example, a C$_6$-C$_{20}$ arylene group or a C$_7$-C$_{20}$ alkylarylene group.

As another example, the (meth)acrylate of the hydroxy aryl (meth)acrylate compound or hydroxy alkylaryl (meth)acrylate compound may be methacrylate or acrylate.

In addition, the hydroxy aryl (meth)acrylate compound or hydroxy alkylaryl (meth)acrylate compound may, for example, be present in an amount of 0.1 to 20 parts by weight, 1 to 15 parts by weight or 5 to 12 parts by weight, based on 100 parts by weight of the organocyclosiloxane.

The reaction for preparing unmodified polyorganosiloxane a) is for example carried out at 50 to 70° C. for 1 to 6 hours.

The reaction for preparing polyorganosiloxane b) is for example carried out at 80 to 100° C. for 1 to 5 hours.

As another example, the method of preparing polyorganosiloxane according to the present invention is carried out in accordance with the following Reaction Scheme 1 below:

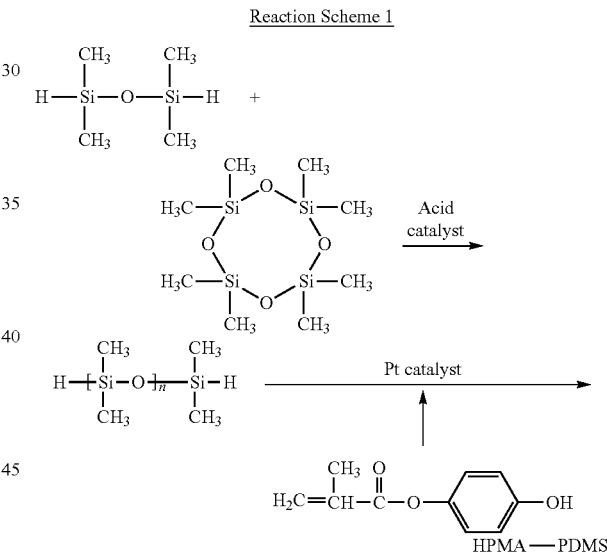

The HPMA-PDMS of Reaction Scheme 1 above is an abbreviation of α,ω-hydroxy phenyl methacrylate functionalized polydimethylsiloxane (α,ω-hydroxy phenyl methacrylate end-capped polydimethylsiloxane).

The modified polycarbonate resin according to the present invention is characterized by a polycarbonate resin modified with the polyorganosiloxane according to the present invention.

For example, the modified polycarbonate resin of the present invention is characterized in being prepared by polymerizing corresponding monomers in the presence of the polyorganosiloxane.

The modified polycarbonate resin for example comprises polyorganosiloxane as a comonomer in a chain.

For example, the modified polycarbonate resin has a weight average molecular weight of 10,000 to 100,000 g/mol, 20,000 to 50,000 g/mol or 30,000 to 40,000 g/mol.

The modified polycarbonate resin for example comprises i) polyorganosiloxane, ii) bisphenol and iii) phosgene or carbonic acid diester.

As another example, the modified polycarbonate resin is prepared by polymerizing the polyorganosiloxane according to the present invention, bisphenol and phosgene.

As another example, the modified polycarbonate resin is prepared by polymerizing the polyorganosiloxane according to the present invention, bisphenol and carbonic acid diester.

The polyorganosiloxane may, for example, be present in an amount of 0.1 to 20% by weight, 1 to 10% by weight, or 2 to 8% by weight, based on 100% by weight in total of the modified polycarbonate resin.

The modified polycarbonate resin for example comprises 10% by weight or less, 5% by weight or less, or 1% by weight or less of free polyorganosiloxane, with respect to 100% by weight in total of the polyorganosiloxane added in the preparation of polycarbonate.

The polycarbonate resin composition according to the present invention comprises the polyorganosiloxane according to the present invention and a polycarbonate resin.

The polycarbonate resin composition for example comprises 0.1 to 20% by weight of the polyorganosiloxane according to the present invention and 80 to 99.9% by weight of the polycarbonate resin. As another example, the polycarbonate resin composition for example comprises 1 to 10% by weight of the polyorganosiloxane according to the present invention and 90 to 99% by weight of the polycarbonate resin. Under these content ranges, advantageously, impact reinforcement and flowability are greatly improved.

Hereinafter, preferred examples will be provided for better understanding of the present invention. These examples are only provided to illustrate the present invention and it will be apparent to those skilled in the art that various modifications and alternations are possible within the scope and technical range of the present invention. Such modifications and alternations fall within the scope of claims included herein.

[Example 1]

<Preparation of Novel Polyorganosiloxane>

Octamethylcyclotetrasiloxane (50 g, 168 mmol) was mixed with tetramethyldisiloxane (2.26 g, 16.8 mmol) and the resulting mixture was reacted with 1 part by weight of an acid clay (DC-A3) with respect to 100 parts by weight of the octamethylcyclotetrasiloxane in a 3 L flask at 60° C. for 4 hours.

After completion of reaction, the reaction solution was diluted with ethyl acetate and rapidly filtered through Celite. A repeat unit of the unmodified polyorganosiloxane thus obtained, determined by $^1$H NMR, was 45.

The obtained unmodified polyorganosiloxane (crude PDMS product) was reacted with BPMA (4-[2-(4-hydroxyphenyl)propan-2-yl]phenyl 2-methylprop-2-enoate, CAS No. 32091-42-2, 9.16 g, 30.9 mmol) in the presence of a Karstedt's platinum catalyst (0.01 g, 50 ppm) at 90° C. for 3 hours. After completion of the reaction, unreacted siloxane was evaporated at 120° C. and 1 torr.

The end-modified polyorganosiloxane (BPMA-capped polydimethylsiloxane; BPMA-PDMS) fluid thus obtained was a pale yellow oil, had a repeat unit of 45 and did not require further purification.

In addition, the preparation of BPMA-PDMS was identified by $^1$H NMR. FIG. 1 is a $^1$H NMR spectrum of the prepared BPMA-PDMS and shows respective hydrogen peaks of BPMA-PDMS.

<Preparation of Polycarbonate Resin Composition and Modified Polycarbonate Resin>

978.4 g of bisphenol A (BPA), 1,620 g of a 32% aqueous NaOH solution and 7,500 g of distilled water were added to a 20 L glass reactor and complete dissolution of the components was observed under a nitrogen atmosphere. Then, the reaction solution was mixed with 3,650 g of methylene chloride, 18.25 g of p-tert-butylphenol and 5.5 g of BPMA-PDMS (5% by weight with respect to the weight of a polycarbonate resin) prepared in Example 1. A solution of 49 g of triphosgene in 3,650 g of methylene chloride was added dropwise to the resulting reaction solution for one hour. At this time, pH of the aqueous NaOH solution was maintained at 12. After dropwise addition, the reaction solution was aged for 15 minutes and a solution of 10 g of triethylamine in methylene chloride was added thereto. After 15 minutes, pH of the reaction solution was adjusted to 3 using a 1N aqueous hydrochloric acid solution, the reaction solution was washed with distilled water three times and the methylene chloride phase was isolated and precipitated in methanol to obtain a powdery modified polycarbonate resin. A molecular weight of the modified polycarbonate resin (PC-PDMS copolymer) thus obtained was measured by GPC using a PC standard and the weight average molecular weight of the modified polycarbonate resin was determined to be 33,000.

[Example 2]

The same process as in Example 1 was repeated except that 5.51 g of HPMA (p-hydroxyphenyl methacrylate, CAS No. 31480-93-0) was used, instead of BPMA, in Example 1.

[Comparative Example 1]

A powdery PC resin was prepared in the same manner as in Example 1, except that the end-modified polyorganosiloxane (BPMA-capped polydimethylsiloxane; BPMA-PDMS) obtained in Example 1 was not used.

[Test Example]

properties of polycarbonate resins prepared in Examples 1 to 2 and Comparative Example 1 were measured in accordance with the following method and the results are shown in Table 1 below.

Weight average molecular weight (g/mol): measured using Agilent 1200 series and calibrated with a PC standard.

Flowability: measured in accordance with ASTM D1238 (under conditions of 300° C. and 1.2 kg).

Impact strength (J/m): measured in accordance with ASTM D256 (⅛ inch, Notched Izod) at 23° C. and −30° C.

Repeat unit: measured by $^1$H-NMR using Varian 500 MHz.

TABLE 1

| | Ex. 1 | Ex. 2 | Comp. Ex. 1 |
|---|---|---|---|
| Weight average molecular weight (g/mol) | 33,000 | 32,500 | 32,000 |
| Flowability | 14 | 13 | 10 |
| Impact strength (J/m, 23° C.) | 910 | 930 | 900 |
| Impact strength (J/m, −30° C.) | 720 | 740 | 170 |

As can be seen from Table 1, the polycarbonate resins (Examples 1 and 2) containing the polyorganosiloxane according to the present invention exhibited similar room-temperature impact strength and transparency, and considerably excellent flowability and low-temperature impact strength, as compared to the polycarbonate resin (Compara-

What is claimed is:

1. Novel polyorganosiloxane represented by Formula 1 below:

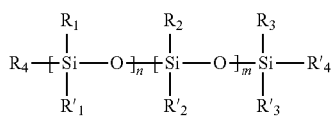

Formula 1 wherein $R_1$ to $R_3$ and $R'_1$ to $R'_3$ represent $CH_3—$ or $C_6H_5—$;

$R_4$ represents

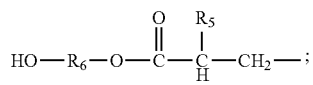

$R'_4$ represents $CH_3—$, $C_6H_5—$ or

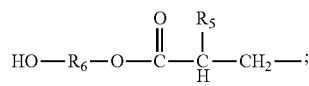

$R_5$ represents H or $CH_3—$;
$R_6$ represents a $C_6$-$C_{20}$ arylene group or a $C_7$-$C_{20}$ alkylarylene group; and
n and m are integers with the proviso of $0 \le n+m \le 99$.

2. The polyorganosiloxane according to claim 1, wherein $R_6$ represents phenylene, diphenylene or dialkylphenylene.

3. A modified polycarbonate resin modified with the polyorganosiloxane according to claim 1.

4. The modified polycarbonate resin according to claim 3, wherein the modified polycarbonate resin comprises the polyorganosiloxane in a chain.

5. The modified polycarbonate resin according to claim 3, wherein the modified polycarbonate resin comprises i) polyorganosiloxane, ii) bisphenol and iii) phosgene or carbonic acid diester.

6. The modified polycarbonate resin according to claim 3, wherein the polyorganosiloxane is present in an amount of 0.1 to 20% by weight, based on 100% by weight of the modified polycarbonate resin.

7. The modified polycarbonate resin according to claim 3, wherein the modified polycarbonate resin has a weight average molecular weight of 10,000 to 100,000.

8. The modified polycarbonate resin according to claim 6, wherein the modified polycarbonate resin comprises 10% by weight of free polyorganosiloxane, with respect to 100% by weight in total of the polyorganosiloxane.

9. A polycarbonate resin composition comprising:
the polyorganosiloxane according to claim 1; and
a polycarbonate resin.

10. The polycarbonate resin composition according to claim 9, wherein the polyorganosiloxane is present in an amount of 0.1 to 20% by weight and the polycarbonate resin is present in an amount of 80 to 99.9% by weight.

* * * * *